United States Patent [19]
Green

[11] Patent Number: 5,885,209
[45] Date of Patent: Mar. 23, 1999

[54] ENDOSCOPIC WORKING CHANNEL AND METHOD OF MAKING SAME

[76] Inventor: Anthony D. Green, 2462 N. Rose, Mesa, Ariz. 85213

[21] Appl. No.: 792,889

[22] Filed: Jan. 31, 1997

Related U.S. Application Data

[60] Provisional application No. 60/011,082 Feb. 2, 1996.
[51] Int. Cl.[6] ...................................................... A61B 1/00
[52] U.S. Cl. ........................... 600/153; 600/123; 600/104
[58] Field of Search ..................... 600/123, 153, 600/154, 139, 140, 104

[56] References Cited

U.S. PATENT DOCUMENTS

| | | | |
|---|---|---|---|
| 3,953,566 | 4/1976 | Gore | 264/288 |
| 4,082,893 | 4/1978 | Okita | 428/376 |
| 4,208,745 | 6/1980 | Okita | 3/1.4 |
| 4,279,245 | 7/1981 | Takagi et al. | 128/4 |
| 4,347,204 | 8/1982 | Takagi et al. | 264/127 |
| 4,676,229 | 6/1987 | Krasnicki et al. | 128/4 |
| 4,753,222 | 6/1988 | Morishita | 600/140 |
| 4,771,766 | 9/1988 | Aoshiro et al. | 128/4 |
| 4,875,468 | 10/1989 | Krauter et al. | 128/3 |
| 5,025,778 | 6/1991 | Silverstein | 128/4 |
| 5,040,543 | 8/1991 | Badera et al. | 128/772 |
| 5,370,108 | 12/1994 | Miura et al. | 128/4 |
| 5,448,988 | 9/1995 | Watanabe | 600/139 |
| 5,460,167 | 10/1995 | Yabe et al. | 600/107 |
| 5,480,423 | 1/1996 | Ravenscroft | 623/1 |
| 5,483,951 | 1/1996 | Frassica et al. | 600/104 |
| 5,529,820 | 6/1996 | Nomi et al. | 600/139 X |

*Primary Examiner*—Beverly M. Flanagan
*Attorney, Agent, or Firm*—David G. Rosenbaum; Sonnenschein Nath & Rosenthal

[57] ABSTRACT

A polytetrafluoroethylene (PTFE) or expanded polytetrafluoroethylene (ePTFE) flexible and bendable working channel section which is circumferentially reinforced against kinking and which is adapted to be insertable, in-line, with the rigid section of the endoscopic working channel.

16 Claims, 2 Drawing Sheets

ENDOSCOPIC WORKING CHANNEL AND METHOD OF MAKING SAME

CROSS-REFERENCE TO RELATED APPLICATION

This application is related to and claims priority from co-pending U.S. Provisional Application Ser. No. 60/011,082 filed Feb. 2, 1996.

BACKGROUND OF THE INVENTION

The present invention relates generally to the field of endoscopy, which includes the use of a tubular structure inserted intraluminally into a mammalian body cavity for visualizing, biopsing and treating tissue regions within the mammalian body.

Various types of endoscopes are known in the art, as exemplified by U.S. Pat. Nos. 4,279,245, 4,676,229, 4,771,766, and 5,483,951. Most types of endoscopes include at least one of a plurality of working channels which extend along the length of the endoscope to provide access to body tissue within the mammalian body. These working channels typically include a rigid non-bendable section and a flexible, bendable section. These channels allow for air insufflation, water flow, suction, and biopsies. Conventional endoscopes utilize a wide variety of materials for the working channels, but all conventional endoscopes require the endoscopic working channel to be an integral part of the endoscope. Because endoscopes are subjected to repeated use and are required to follow tortuous pathways within the body, a frequent cause of failure of the endoscopic working channel is the bending, kinking or fracture of a section of the working channel which renders the endoscope useless until repaired. Unfortunately, repair of the endoscopic working channel requires disassembly of the endoscope and replacement of the endoscopic working channel. Conventional endoscopic working channels are not designed to be retrofitted with replacement bendable sections of the working channel.

SUMMARY OF THE INVENTION

It is, therefore, a principal object of the present invention to provide a replacement flexible and bendable section of the endoscopic working channel which is well-adapted for retrofit and repair of failed endoscopic working channels. The inventive endoscopic working channel is configured to be insertable, in-line, with the existing section of the rigid, non-bendable section of the working channel for repair of the endoscope.

It is a further object of the present invention to provide a microporous expanded polytetrafluoroethylene (ePTFE) flexible and bendable working channel section which is circumferentially reinforced against kinking and which is adapted to be insertable, in-line, with the rigid section of the endoscopic working channel.

DETAILED DESCRIPTION OF THE PREFERRED EMBODIMENTS

Figure 1:
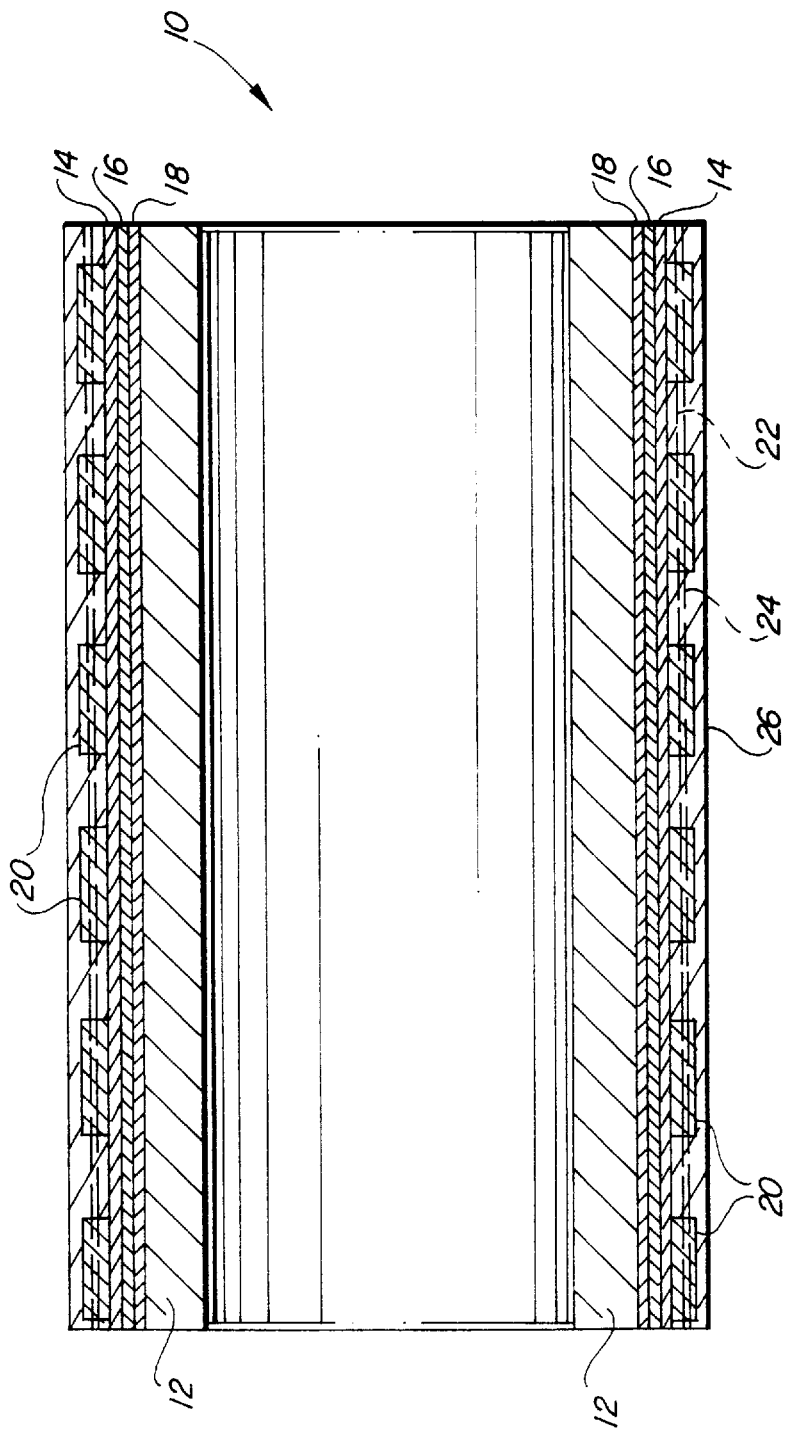
FIG. 1 is a diagrammatic axial cross-sectional view of the inventive endoscopic working channel.

As illustrated in FIG. 1, the inventive endoscopic working channel 10 consists generally of a tubular structure 12 fabricated from polytetrafluoroethylene, which may be either non-expanded polytetrafluoroethylene (PTFE) or expanded polytetrafluoroethylene (ePTFE) of the type generally described in U.S. Pat. No. 4,187,390, which is hereby incorporated by reference as teaching methods of fabricating microporous ePTFE. It is preferable that the polytetrafluoroethylene tubular structure 12 have a density within the range of 0.8–2.2 g/cc. The polytetrafluoroethylene tubular structure 12 has a biocompatible elastomer impregnated into the microporous microstructure and a first circumferential covering of at least one of a plurality of layers of an elastomer 14, 16, 18, a helical winding of a flat ribbon wire 20, preferably made of stainless steel, applied over the first circumferential covering of the at least one of a plurality of layers of elastomer 14, 16, 18, and a second circumferential covering of at least one of a plurality of layers of an elastomer 22, 24, 26. In accordance with the preferred embodiments and the best mode for practicing the invention, the first circumferential covering of at least one of a plurality of layers of elastomer 14, 16, 18 consists of a polyurethane dispersion, drape coated onto the tubular structure 12, according to the inventive method to be described hereinafter.

Biocompatible elastomers suitable for use with the present invention consist of medicalgrade silicone rubber elastomers, segmented polyurethanes, polyurethane-ureas and siliconepolyurethane copolymers.

Each of the opposing ends (not shown) of the inventive endoscopic working channel 10 may be finished by applying a wrap of polytetrafluoroethylene tape, or a heat shrinkable tube made of polyolefm or polytetrafluoroethylene, co-terminus with each opposing end of the inventive endoscopic working channel 10 and covering terminal ends of the helical flat ribbon wire.

Alternatively, one or both of the opposing ends of the PTFE or ePTFE tube 12 may be chemically etched, using a etchant suitable for use with polytetrafluoroethylene, such as that sold under the trademark FLUOROETCH or TETRAETCH (W.L. Gore Associates). Chemical etching facilitates subsequent adhesive bonding of the etched end with a section of an original endoscopic working channel in an endoscope to be retrofit with the present invention. In a first embodiment of the present invention a first end of the ePTFE tube, specifically, that end which is intended to be the distal end of the inventive endoscopic working channel is chemically etched in order to increase the capacity of the PTFE or ePTFE tube 12 to accept an adhesive bond with a distal section of an endoscope, while a second end of the PTFE or ePTFE tube 12, specifically, that end which is intended to be the proximal end of the inventive endoscopic working channel is not etched, as it will be mechanically coupled to a proximal section of an endoscope. In a second embodiment of the present invention, which is specifically useful where the inventive endoscopic working channel is intended to be positioned in an intermediate region of an endoscopic working channel of an endoscope, both the first and second ends of the inventive endoscopic working channel are preferably chemically etched in order to increase their capacity to be adhesively bonded to the pre-existing working channel of the endoscope. In each of the first and second embodiments of the present invention, each of the opposing ends of the inventive endoscopic working channel 10 may be finished by trimming the ends such that the flat ribbon wire and the plurality of elastomeric layers 14, 16, 18, 22, 24, 26 extend to a point co-terminus with each opposing end of the endoscopic working channel 10.

As will be illustrated by the following description of the method of making the endoscopic working channel 10, in accordance with the best mode of practicing the invention, it has been found preferable to apply a first layer 14 of elastomer by dip coating PTFE or ePTFE tubing 12, then, if an ePTFE tube 12 is employed, placing the dip coated ePTFE tube 12 into a vacuum chamber to withdraw air resident in the interstices of the microporous node and fibril material matrix of the ePTFE. This first layer of elastomer then serves as a base bonding layer for the subsequent layers 16, 18 of elastomer forming the first circumferential covering.

Figure 2:
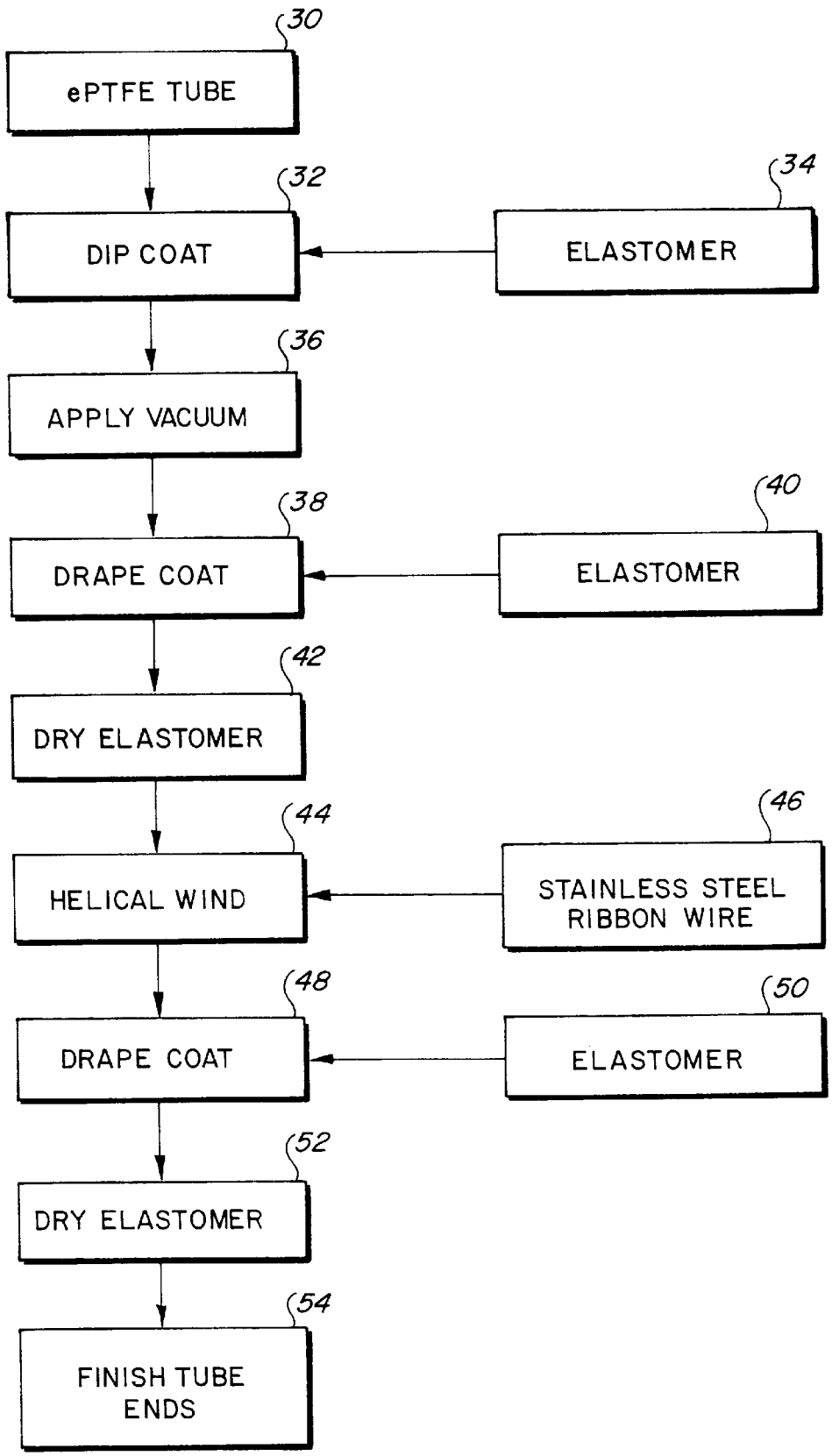
FIG. 2 is a process flow diagram illustrating the method used to fabricate the inventive endoscopic working channel.

In accordance with the preferred embodiment of the present invention, and with reference to FIG. 2, the method of making the endoscopic working channel 10 consists of the following steps, all of which may be conducted at room temperature:

1. PTFE or ePTFE tubing is provided at step 30. Both PTFE and ePTFE tubing may made in accordance with well known methodologies. Expanded PTFE materials are characterized by a microporous microstructure consisting of nodes interconnected by fibrils with the fibril orientation being parallel to the axis of expansion. Interstices between adjacent nodes form open microporous structures in the material matrix of the ePTFE. The inner diameter of the ePTFE tubing is preferably selected to match those required for a particular endoscope, and may be, for example, 2.8 mm, 3.2 mm, 3.7 mm or 4.2 mm to match the inner diameters of the endoscopic working channels which the present invention is intended to replace.

2. The PTFE or ePTFE tubing is then dip coated at step 32 with a liquid elastomer solution 34. It is preferable to provide a liquid elastomer dispersion solution which has been subjected to a vacuum to eliminate air in the dispersion. In accordance with the best mode of the present invention, a 4% solids polyurethane in solution with 80% tetrahydrofuran (THF) and 20% dimethylformamide (DMF) is prepared as a dip coat for the PTFE or ePTFE tubing. A 4% solids polyurethane solution has been found to meet the competing requirements of ease of impregnation into ePTFE tubing, while being resistant to agglomeration of the polyurethane solid and dripping. The dip coating solution may, alternatively, be a 2.5 to 7% solids polyurethane solution, but it has been found that about a 4% solids polyurethane solution provides the best results. All percentages are expressed herein as weight percents. To facilitate dip coating and subsequent handling of the PTFE or ePTFE tubing, it is preferable to pre-mount the tubing onto appropriately sized mandrels.

3. Where ePTFE tubing is employed, the ePTFE tubing in the dip coating polyurethane solution is then placed in a vacuum jar and air resident in the interstices of the microporous material matrix is evacuated at step 36. Evacuation at approximately 15–20 in Hg vacuum, preferably 16–18, for a period of time sufficient to draw off substantially all of the air in the ePTFE, which has been found to be approximately 3–20 minutes at room temperature, has been found sufficient to bond the 4% elastomer solution to the ePTFE tubing. The point at which the air is substantially drawn off the ePTFE is observable by the translucent nature of the ePTFE. After vacuum treatment, the elastomer coated ePTFE tubing is air dried to drive off the solvent.

4. The dried elastomer coated PTFE or ePTFE tubing is then drape coated 38 with two subsequent coats of elastomer solution 40. Drape coating is accomplished by passing the elastomer solution 40 longitudinally over the PTFE or ePTFE tubing, and drying 42 the solvent between coats of elastomer solution 40. It has been found preferable to utilize a 12% solids polyurethane dispersion solution in 80% THF and 20% DMF for the two subsequent coatings. The drape coat may, alternatively, consist of a 10 to 18% solids polyurethane solution, but is preferably provided as about a 12% solids polyurethane solution. Lower concentrations of polyurethane solids decreases the viscosity of the solution and increases its ability to flow during coating. This may be compensated for by decreasing the tolerances during the coating process. Higher concentrations of polyurethane solids has been found to increase the viscosity of the solution and reduces the rate at which the drape coat may be applied, thereby, increasing the processing time. The 12% solids polyurethane solution has been found to provide an optimum balance between the need to provide a proper thickness to the elastomer drape coat, process speed and uniformity of elastomer layer thickness. To facilitate ease of drape coating the PTFE or ePTFE tubing, the elastomer solution is introduced into a cup which has a central annular opening passing through the cup bottom. The central annular opening in the cup bottom is appropriately sized to permit the PTFE or ePTFE tubing to pass through the opening in close abutment to the lateral surfaces of the annular opening while providing resistance to leakage of the elastomer solution at the interface between the PTFE or ePTFE tubing and the annular opening. Either the cup or the tubing may be movable such that either the cup passes along the longitudinal axis of the tubing or the tubing is drawn through the annular opening. The first drape coat of elastomer solution is dried onto the PTFE or ePTFE tubing.

5. A helical winding 44 of a flat ribbon wire 46, which is preferably made of stainless steel, is then applied circumferentially over the first circumferential elastomer coating on the PTFE or ePTFE tubing. For example, it has been found that a flat stainless steel ribbon wire having a thickness of 0.003 in. and a width of 0.025 in. is well suited for use with the present invention.

6. Three additional coats 22, 24, 26 of elastomer 50 are drape coated 48 over the helically wound stainless steel wire and PTFE or ePTFE tubing, in the same manner as in step 38 above. Again, it is preferable to employ a 12% solids polyurethane dispersion solution as the drape coat, with drying steps 52 between successive coats of elastomer 50.

7. Finally, opposing ends of the elastomer coated ePTFE tube may be finished by applying a helical wind or tubular material, preferably a heat shrinkable plastic over each end of the elastomer ePTFE tube to facilitate attachment in-line with the rigid working channel of the endoscope. Alternatively, and in accordance with the best mode contemplated for practicing the present invention, the proximal and distal ends of the elastomer coated ePTFE tube may simply be trimmed and free of additional material or wraps.

In accordance with the best mode for practicing the invention, it is preferable that each layer in the first set of circumferential layers and the second set of circumferential layers, formed from the same concentration of elastomer dispersion solution, have substantially equal thicknesses and uniform thickness along the longitudinal axis of the ePTFE tube.

Those skilled in the art will understand and appreciate that variations in materials, concentrations, dimensions, or the like may be made without departing from the scope of the present invention which is intended to be limited only by the claims appended hereto. For example, alternative biocompatible elastomers may be employed, various porosity ePTFE may be employed, alternative concentrations of elastomer solution may be employed, or alternative coating methadologies may be followed so long as the ePTFE tubing has a regular and even coating of elastomer thereupon.

What is claimed is:

1. An endoscopic working channel capable of retrofit into a pre-existing endoscope, comprising:
   a) an expanded polytetrafluoroethylene tubular member having a microporous microstructure and having first and second opposing ends, an intermediate section and luminal and abluminal wall surfaces thereof;
   b) an elastomer impregnated into the microporous microstructure of the expanded polytetrafluoroethylene tubular member;
   c) a first elastomer layer circumferentially provided on at least a substantial longitudinal extent of the the ablumenal wall suface of the expanded polytetrafluoroethylene tubular member;
   d) a circumferential support positioned about the first elastomer layer; and
   e) at least one additional elastomer layer provided about and covering the circumferential support.

2. The endoscopic working channel according to claim 1, wherein the elastomer impregnated into the microporous microstructure further comprises polyurethane.

3. The endoscopic working channel according to claim 1, wherein the first elastomer layer further comprises polyurethane.

4. The endoscopic working channel according to claim 3, wherein the first elastomer layer further comprises a 2.5 to 7% solids by weight polyurethane solution.

5. The endoscopic working channel according to claim 4, wherein the first elastomer layer further comprises about 4% solids by weight polyurethane solution.

6. The endoscopic working channel according to claim 1, wherein the circumferential support further comprises flat ribbon wire.

7. The endoscopic working channel according to claim 6, wherein the flat ribbon wire is helically wrapped about the circumference of the expanded polytetrafluoroethylene tubular member and passes along at least a substantial longitudinal extent thereof.

8. The endoscopic working channel according to claim 1, wherein the at least one additional elastomer layer provided about and covering the circumferential support further comprises polyurethane.

9. The endoscopic working channel according to claim 8, wherein the at least one additional elastomer layer further comprises a 10 to 17% solids by weight polyurethane solution.

10. The endoscopic working channel according to claim 5, wherein the at least one additional elastomer layer further comprises about 12% solids by weight polyurethane solution.

11. An endoscopic working channel capable of retrofit into a pre-existing endoscope, comprising:
    a) a polytetrafluoroethylene tubular member having a microporous microstructure and having first and second opposing ends, an intermediate section and luminal and abluminal wall surfaces thereof;
    b) a first polyurethane elastomer layer circumferentially provided on at least a substantial longitudinal extent of the abluminal wall surface of the polytetrafluoroethylene tubular member;
    c) at least one flat ribbon wire member circumferentially positioned about the first elastomer layer and extending about at least a substantial longitudinal extent of the polytetrafluoroethylene tubular member; and
    d) at least one additional polyurethane elastomer layer provided about and covering the circumferential support.

12. The endoscopic working channel according to claim 11, wherein the polytetrafluoroethylene tubular member further comprises expanded polytetrafluoroethylene.

13. The endoscopic working channel according to claim 11, wherein the first elastomer layer further comprises a 2.5 to 7% solids by weight polyurethane solution.

14. The endoscopic working channel according to claim 12, wherein the first elastomer layer further comprises about 4% solids by weight polyurethane solution.

15. The endoscopic working channel according to claim 12, wherein the at least one additional elastomer layer further comprises a 10 to 17% solids by weight polyurethane solution.

16. The endoscopic working channel according to claim 14, wherein the at least one additional elastomer layer further comprises about 12% solids by weight polyurethane solution.

* * * * *